United States Patent [19]

Stromberg

[11] Patent Number: 5,741,294

[45] Date of Patent: Apr. 21, 1998

[54] METHOD OF FIXSANGUINATION OF A LIMB

[76] Inventor: Brent B. Stromberg, 450 N. New Ballas Rd., Suite 250, St. Louis, Mo. 63141

[21] Appl. No.: 803,778

[22] Filed: Feb. 24, 1997

Related U.S. Application Data

[63] Continuation of Ser. No. 634,361, Apr. 18, 1996, abandoned, which is a continuation of Ser. No. 337,972, Nov. 14, 1994, abandoned.

[51] Int. Cl.$^6$ ........................................................ A61H 1/00
[52] U.S. Cl. ............................................................ 606/201
[58] Field of Search ................................. 606/201–203; 128/677, 685, 686, DIG. 20

[56] References Cited

U.S. PATENT DOCUMENTS

| | | | |
|---|---|---|---|
| 3,862,629 | 1/1975 | Rotta | 128/DIG. 20 |
| 4,013,069 | 3/1977 | Hasty | 128/DIG. 20 |
| 4,066,084 | 1/1978 | Tillander | 606/202 |
| 4,198,961 | 4/1980 | Arkans . | |
| 4,793,328 | 12/1988 | Kolstedt et al. | 128/DIG. 20 |
| 5,179,941 | 1/1993 | Siemssen et al. | 606/201 |

FOREIGN PATENT DOCUMENTS

| | | | |
|---|---|---|---|
| 0327879 | 8/1989 | European Pat. Off. | 606/202 |

*Primary Examiner*—Michael Buiz
*Assistant Examiner*—William Lewis
*Attorney, Agent, or Firm*—Frank B. Janoski; Michael T. Marrah

[57] ABSTRACT

A device for the cessation of the blood flow in an extremity comprising a plurality of chambers encircling the extremity in a sequential arrangement. Each chamber being able to individually apply or release pressure to the extremity. The device has a monitor for determining the pressure applied to the extremity. The device further having a mechanism for continuously cycling the chambers.

1 Claim, 1 Drawing Sheet

METHOD OF FIXSANGUINATION OF A LIMB

This application is a continuation of application Ser. No. 08/634,361, filed Apr. 18, 1996, now abandoned, which is a continuation of application Ser. No. 08/337,972 filed Nov. 14, 1994 now abandoned.

BACKGROUND OF THE INVENTION

This invention relates generally to an improvement in the cessation of blood flow and removal of blood in an extremity, and more particularly to a device which continuously cycles its chambers.

This invention is in the same general field as the pneumatic exsanguination and method for exsanguinating a limb disclosed in U.S. Pat. No. 4,781,189, issued Nov. 1, 1988.

SUMMARY OF THE INVENTION

Among the several objects of this invention may be noted the provision of a sequential tourniquet which can easily be used on an arm or leg; the provision of a sequential tourniquet which is relatively simply, safe and convenient to use; a sequential tourniquet which causes less trauma to the extremity and less pain and damage to the patient; the provision of a sequential tourniquet that permits the return of circulation to the extremity if the surgery is prolonged and that can easily reapply pressure to the extremity; and a sequential tourniquet that can be continuously cycled.

In general, a device of the present invention for the cessation of blood flow in an extremity consists of a plurality of chambers encircling the extremity in a sequential arrangement. Each chamber has a means for applying pressure to the extremity and means for releasing the pressure applied to the extremity by each chamber. The device also has means to monitor the pressure applied to the extremity by each chamber and means for continuously cycling the chambers.

Other objects and features will be in part apparent and in part pointed out here and after.

DESCRIPTION OF THE PREFERRED EMBODIMENT

Figure 1:
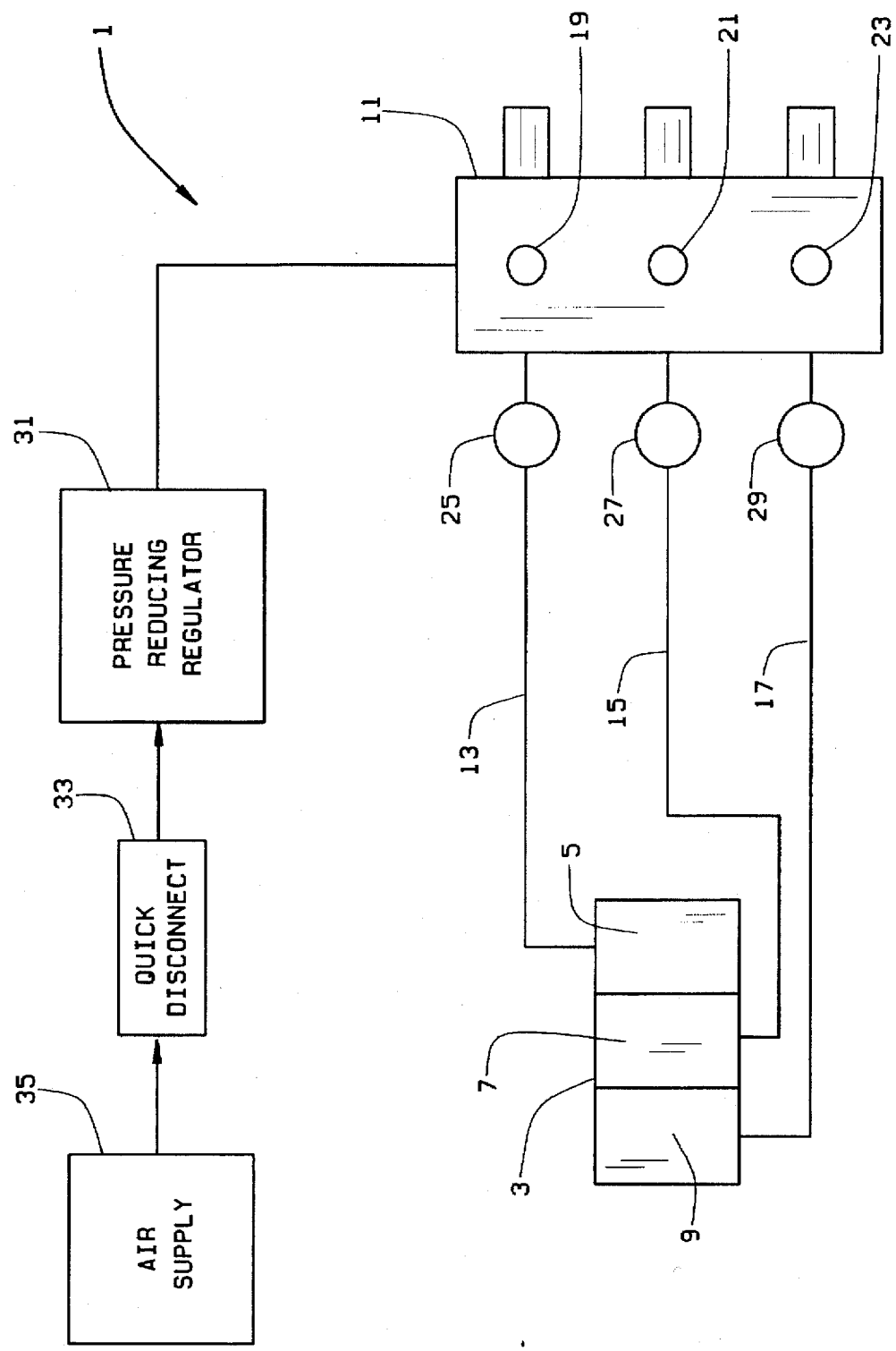
FIG. 1 is a simplified block diagram representation of this invention.

Referring to FIG. 1, there is generally indicated at 1 a block diagram of a sequential tourniquet of this invention for a pneumatic powered device. It will be understood that the description and illustration are not intended to limit the invention which can be activated electronically, mechanically or by other methods.

As shown in the drawing, the sequential tourniquet 3 has three chambers 5, 7 and 9, which are designed to encircle an extremity, such as an arm or a leg and constitute means for applying pressure to the extremity. The tourniquet and the chambers can be of any size and shape. Moreover, the chambers do not need to be connected to each other (i.e., such as a single piece); however, this is the preferred configuration in order to maximize control of the flow of blood to the extremity as will be understood by those familiar in the art.

The chambers 5, 7 and 9 are connected to a solenoid valve 11, of other suitable type of valve, by hoses 13, 15 and 17, respectively. The solenoid valve 11 shown is a three-way valve which can be vented as indicated by vent ports 19, 21 and 23 or the like and constitute means for releasing the pressure applied on one extremity by each chamber. The solenoid valve 11 can be a micro process base controller with nonvolatile RAM memory. On the downstream side of the solenoid valve are pressure switches 25, 27 and 29 for the chambers and constitute means to monitor the pressure applied to the extremity by each chamber. As will be understood by those familiar in the art, these switches are not necessary to the invention but are appropriate if there is concern for damage to the tissue.

On the upstream side of the solenoid valve is a pressure reducing regulator 31 (a Brooks Model Number 8601D1A1AA, high performance regulator can be used) and a quick disconnect valve 33. An air supply 35, such as a container of compressed air or nitrogen or other gases from any other source, is provided to inflate the chambers of the tourniquet as will be understood by those familiar in the art.

Although not shown, it will be understood by those familiar in the art that a timing device may be appropriately connected to the solenoid valves so that the chambers would be inflated and deflated at predetermined intervals in order to increase the comfort of the patient and constitute means for continuously cycling the chambers. This procedure would result in the tourniquet acting similar to a roller pump to maintain or decrease fluid volume in the extremity.

In operation, the air supply is connected at the quick disconnect. (However, it will be understood that the air supply may be connected in various other ways.) The sequential tourniquet is positioned at the desired points on the extremity, such as the upper and lower arm, of the patient. It is preferred that the tourniquet have been pre-connected and pre-tested for leaks before operating this device. The timing device is set for sequential pressurization and deflation of each chamber at predetermined intervals. It will be understood that one chamber should be fully pressurized prior to deflation of the previously pressurized chamber. (Of course, the inflation and deflation of the chambers may be done manually if desired.) Thus, the chambers of the tourniquet are alternately, and automatically, inflated and deflated. This decreases the number of personnel required for surgical procedures and increases the comfort of the patient.

As an example, the microprocessor can be set such that the solenoid will pressurize chamber 5 at a count of 0.01 seconds and deactivate chamber 5 at 0.06 seconds. The solenoid then could pressurize chamber 7 at 0.07 seconds and deactivate chamber 7 at 0.12 seconds. The solenoid then could pressurize chamber 9 at 0.13 seconds and deactivate chamber 9 at 0.18 seconds. This sequence would then repeat itself for as long as necessary. Moreover, the 0.05 second interval can be varied as needed based upon the location of the chambers and the procedure to be performed. (It also will be understood that the cycling may be halted and the pressure maintained if desired.)

In view of the above, it will be seen that the several objects of the invention are achieved and other advantageous results attained.

As various changes could be made in the above construction without departing from the scope of the invention, it is intended that all matter contained in the above description and as shown in the company drawings shall be interpreted as illustrative and not in a limiting sense.

What is claimed is:

1. A method of exsanguination of a limb, comprising the steps of:

a) placing an unpressurized, multichambered tourniquet with substantially parallel and adjacent chambers around the limb proximal to and not covering the site to be exsanguinated;

b) pressurizing the most distal chamber to a pressure sufficient to stop the flow of blood in the limb;

c) maintaining the pressure in the most distal chamber while pressuring the adjacent chamber to substantially the same pressure as the most distal chamber;

d) maintaining the pressure in at least the most recently pressurized chamber while pressurizing the next proximal and adjacent chamber to substantially the same pressure as the most distal chamber;

e) repeating the above step until the most proximal chamber is pressurized;

f) maintaining the pressure of the most proximal chamber while the distal chambers are depressurized to allow any blood remaining in the distal part of the limb to flow under the distal chambers;

g) pressurizing the most distal chamber to a pressure sufficient to stop the flow of blood in the limb;

h) depressurizing the most proximal chamber;

i) repeating steps c–h, above, until degree of exsanguination is achieved; and j) maintaining the exsanguination by slowing the cycling action of the chambers or by stoping the cycling action of the chambers and leaving at least one chamber pressurized to a level sufficient to prevent the flow of blood into the exsanguinated portion of the limb.

* * * * *